United States Patent
van Kesteren (10) Patent No.: US 12,426,787 B2
(45) Date of Patent: Sep. 30, 2025

(54) METHODS AND SYSTEMS FOR CAPNOGRAPY SIGNAL PROCESSING

(71) Applicant: KONINKLIJKE PHILIPS N.V., Eindhoven (NL)

(72) Inventor: Hans Willem van Kesteren, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 715 days.

(21) Appl. No.: 17/635,485

(22) PCT Filed: Nov. 13, 2020

(86) PCT No.: PCT/EP2020/082001
§ 371 (c)(1),
(2) Date: Feb. 15, 2022

(87) PCT Pub. No.: WO2021/099216
PCT Pub. Date: May 27, 2021

(65) Prior Publication Data
US 2022/0330827 A1     Oct. 20, 2022

(30) Foreign Application Priority Data
Nov. 22, 2019  (EP) ..................... 19210928

(51) Int. Cl.
*A61B 5/00*        (2006.01)
*A61B 5/083*       (2006.01)

(52) U.S. Cl.
CPC .......... *A61B 5/0075* (2013.01); *A61B 5/0836* (2013.01); *A61B 5/7235* (2013.01)

(58) Field of Classification Search
CPC ... A61B 5/0075; A61B 5/7235; A61B 5/7203; A61B 5/0836; A61B 2560/0238
See application file for complete search history.

(56) References Cited

U.S. PATENT DOCUMENTS 7,192,782 B2   3/2007  Roller
9,546,902 B2 *  1/2017  Kovacich ................ G01J 3/027
(Continued)

FOREIGN PATENT DOCUMENTS

| JP | 2001066254 A | 3/2001 |
|----|--------------|--------|
| JP | 2001133403 A | 5/2001 |
| WO | 2010106064 A1 | 9/2010 |

OTHER PUBLICATIONS

Roller, C.B. et al., "Measurement of Exhaled Nitric Oxide in Beef Cattle Using Tunable Diode Laser Absorption Spectroscopy", Applied Optics, Optical Society of America, Washington, DC, vol. 46, No. 8 (Mar. 10, 2007).

(Continued)

*Primary Examiner* — An H Do (57) ABSTRACT

The invention provides a method for obtaining a filtered capnography signal by suppressing a spectral background signal within an optical absorption signal. An optical absorption signal is obtained from a subject across a range of wavelengths, wherein the optical absorption signal represents a proportion of a light signal that is absorbed as the light signal passes through a respiratory air sample undergoing investigation, and wherein the optical absorption signal comprises a spectral background signal. A second harmonic signal is isolated from the optical absorption signal and the period of the spectral background signal is identified. The second harmonic signal is sampled at a central wavelength of the second harmonic signal, wherein the central wavelength represents a maximum Carbon Dioxide absorption, an at an off-center wavelength of the second harmonic signal, wherein the off-center wavelength and the central wavelength are separated by a multiple of the period (Continued)

of the spectral background signal. A filtered capnography signal is then generated based on the sampled second harmonic signal.

13 Claims, 6 Drawing Sheets

(56) References Cited

U.S. PATENT DOCUMENTS

| | | | | |
|---|---|---|---|---|
| 11,331,004 B2* | 5/2022 | Causevic | ............... | A61B 5/097 |
| 11,692,934 B2* | 7/2023 | Normand | .............. | G01J 3/0229 |
| | | | | 356/437 |
| 2011/0302992 A1 | 12/2011 | Robbins | | |

OTHER PUBLICATIONS

Lu, C. et al., "Condensed Matter: Electronic Structure, Electrical, Magnetic, and Optical Properties; Calibration-free wavelength modulation spectroscopy for gas concentration measurements under low-absorbance conditions", Chinese Physics B, Bristol GB, vol. 21, No. 12 (Dec. 11, 2012), p. 127803.
Roller, C. et al., "Nitric oxide breath testing by tunable-diode laser absorption spectroscopy: application in monitoring respiratory inflammation", Applied Optics, vol. 41, No. 28 (Oct. 1, 2002), p. 6018.
International Search Report for PCT/EP2020/082001 filed Nov. 13, 2020.

\* cited by examiner

METHODS AND SYSTEMS FOR CAPNOGRAPY SIGNAL PROCESSING

CROSS-REFERENCE TO PRIOR APPLICATIONS

This application claims the priority benefit under 35 U.S.C. § 371 of International Patent Application No. PCT/EP2020/082001, filed on Nov. 13, 2020, which claims the priority benefit of European Patent Application No. 19210928.8 filed on Nov. 22, 2019, the contents of which are herein incorporated by reference.

FIELD OF THE INVENTION

This invention relates to the field of signal processing in capnography sensors with a laser source, and more specifically to the field of suppressing a spectral background signal in a capnography signal.

BACKGROUND OF THE INVENTION

Capnography devices are used to monitor the $CO_2$ concentration in air exhaled by a subject. Capnography sensors measure the $CO_2$ concentration by detecting an amount of optical light absorption in the exhaled air. The light is typically generated by a thermal mid-infrared light source. However, capnography devices with a mid-infrared light source have a high power consumption and large device size because they incorporate a pump and are typically connected to a sampling tube to transport part of the respiratory air towards the optical $CO_2$ detection unit in the capnography device.

A capnography device with a diode laser and the application of an optical fiber to guide the light for the $CO_2$ detection from the laser source to the oral-nasal cannula, or the airway adapter in a ventilation circuit, offers advantages in providing a small form factor, low power consumption and offers detection without delay and smearing of the waveform as present in current sidestream capnography devices.

A capnography device with an optical fiber may use a tunable near-infrared diode laser as the light source. In the near-infrared range, fiber technology is well developed in contrast to the mid-infrared range; however, $CO_2$ absorption is much smaller in the near-infrared than in the mid-infrared. Wavelength modulation and lock-in detection is commonly used in tunable diode laser absorption spectroscopy (TDLAS) to improve the signal-to-noise ratio of the small absorption signals in the near-infrared range.

An ongoing issue in laser based capnography devices is the presence of spectral background signals, which lead to capnography signal quality degradation by interference effects resulting from reflections on surfaces of optical components in the light path.

There is therefore a need to suppress the spectral background signals in laser based capnography systems.

SUMMARY OF THE INVENTION

The invention is defined by the claims.

According to examples in accordance with an aspect of the invention, there is provided a method for obtaining a filtered capnography signal by suppressing a spectral background signal within an optical absorption signal, the method comprising:

obtaining an optical absorption signal from a subject across a range of wavelengths, wherein the optical absorption signal represents a proportion of a light signal that is absorbed as the light signal passes through a breathing adapter containing a respiratory air sample undergoing investigation, and wherein the optical absorption signal comprises a spectral background signal;

isolating a second harmonic signal from the optical absorption signal;

identifying a period of the spectral background signal;

sampling a plurality of wavelength components of the second harmonic signal, wherein sampling the second harmonic signal comprises:

obtaining a sample of the second harmonic signal at a central wavelength of the second harmonic signal, wherein the central wavelength represents a maximum Carbon Dioxide absorption; and obtaining a sample of the second harmonic signal at an off-center wavelength of the second harmonic signal, wherein the off-center wavelength and the central wavelength are separated by a multiple of the period of the spectral background signal; and generating a filtered capnography signal based on the sampled second harmonic signal.

The method provides for a means of suppressing a spectral background signal in a capnography signal that is robust against interference, such as temperature fluctuations, as the period of the spectral background signal does not vary significantly.

By performing the suppression of the spectral background signal based on the period of the spectral background signal, the suppression is independent of wavelength shifts in the spectral background signals, which otherwise reduces the accuracy of typical filtering methods. Further, the resulting filtered signal is also independent of the spectral background intensity, meaning that an accurate filtered second harmonic signal may be obtained regardless of the level of spectral background present in the originally acquired capnography signal.

In an embodiment, the multiple of the period of the spectral background signal is a multiple of a full period of the spectral background signal.

In an embodiment, the multiple of the period of the spectral background signal is a multiple of a half period of the spectral background signal.

In an embodiment, obtaining the sample of the second harmonic signal at the central wavelength is performed over a first time period and obtaining the sample of the second harmonic signal at the off-center wavelength is performed over a second time period, wherein the first time period and the second time period are equal in length.

In this way, a significant proportion of the sampling time is directed towards sampling the central wavelength of the second harmonic signal, thereby maintaining the accuracy of the $CO_2$ detection whilst also suppressing the spectral background signal.

In an embodiment, sampling the second harmonic signal further comprises obtaining a plurality of samples of the second harmonic signal at a plurality of off-center wavelengths of the second harmonic signal, wherein the plurality of off-center wavelengths and the central wavelength are separated by multiples of the period of the spectral background signal.

In this way, the suppression of the spectral background signal may further account for changes in the period of the spectral background signal.

In a further embodiment, the sample of the second harmonic signal at the central wavelength is performed over a first time period and obtaining the plurality of samples of the second harmonic signal at the plurality of off-center wavelengths is performed over a second time period, wherein the first time period and the second time period are equal in length.

In this way, a significant proportion of the sampling time is directed towards sampling the central wavelength of the second harmonic signal, thereby maintaining the accuracy of the $CO_2$ detection whilst also suppressing the spectral background signal.

In an embodiment, the method further comprises:
isolating a third harmonic signal from the optical absorption signal;
sampling a plurality of wavelength components of the third harmonic signal, wherein sampling the third harmonic signal comprises:
obtaining a sample of the third harmonic signal at a central wavelength of the third harmonic signal; and
obtaining a sample of the third harmonic signal at an off-center wavelength of the third harmonic signal, wherein the off-center wavelength and the central wavelength are separated by a multiple of the period of the spectral background signal; and
generating a wavelength correction for the central and off-center wavelengths.

In this way, the spectral background may be suppressed in the third harmonic signal of the capnography signal and a wavelength correction for the capnography signal may be generated.

In an embodiment, the method is for use in processing an optical absorption signal obtained from a breathing cycle of a subject.

In a further embodiment, the period of the spectral background signal is identified during an inhalation phase of the breathing cycle.

In this way, the spectral background may be identified in air having a relatively low $CO_2$ concentration, when compared to air exhaled by the subject, meaning that the spectral background signal is more pronounced and so the accuracy of the identified period may be increased.

In a further embodiment, the period of the spectral background signal is identified by averaging over a plurality of breathing cycles.

In this way, the accuracy of the identified period may be further increased.

In an embodiment, the method further comprises obtaining a separate background signal, wherein the spectral background period is identified from the separate background signal.

In this way, the accuracy of the identified period may be further increased.

According to examples in accordance with an aspect of the invention, there is provided a computer program comprising computer program code means which is adapted, when said computer program is run on a computer, to implement the methods described above.

According to examples in accordance with an aspect of the invention, there is provided a system for obtaining a filtered capnography signal by suppressing a spectral background signal within an optical absorption signal, the system comprising:
a processor, wherein the processor is adapted to:
obtain an optical absorption signal from a subject across a range of wavelengths, wherein the optical absorption signal represents a proportion of a light signal that is absorbed as the light signal passes through a breathing adapter containing a respiratory air sample undergoing investigation, and wherein the optical absorption signal comprises a spectral background signal;
isolate a second harmonic signal from the optical absorption signal;
identify a period of the spectral background signal;
sample a plurality of wavelength components of the second harmonic signal, wherein sampling the second harmonic signal comprises:
obtain a sample of the second harmonic signal at a central wavelength of the second harmonic signal, wherein the central wavelength represents a maximum Carbon Dioxide absorption; and
obtain a sample of the second harmonic signal at an off-center wavelength of the second harmonic signal, wherein the off-center wavelength and the central wavelength are separated by a multiple of the period of the spectral background signal; and
generate a filtered capnography signal based on the sampled second harmonic signal.

In an embodiment, the system further comprises:
a processor as described above;
a wavelength tunable laser light source adapted to generate a laser light signal that is modulated across a range of wavelengths, and wherein the processor is further adapted to isolate the second harmonic signal using a frequency of the modulation of the light source as a reference;
an optical fiber in communication with the wavelength tunable laser light source;
a breathing adapter having a cavity adapted to be connectable to an airway of a subject, the breathing adapter being in communication with the optical fiber such that the laser light signal enters the cavity; and
a light detector, in communication with the cavity of the breathing adapter and adapted to receive the laser light signal transmitted through the cavity.

In an embodiment, one or more of:
the modulation depth of the light source; and
a dimension of the breathing adapter, is adjusted, thereby adjusting the spectral background period, in order to align the spectral background period with a maximum and a minimum of second harmonic signal.

These and other aspects of the invention will be apparent from and elucidated with reference to the embodiment(s) described hereinafter.

BRIEF DESCRIPTION OF THE DRAWINGS

Examples of the invention will now be described in detail with reference to the accompanying drawings, in which.

DETAILED DESCRIPTION OF THE EMBODIMENTS

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a method for obtaining a filtered capnography signal by suppressing a spectral background signal within an optical absorption signal. An optical absorption signal is obtained from a subject across a range of wavelengths, wherein the optical absorption signal represents a proportion of a light signal that is absorbed as the light signal passes through a breathing adapter containing a respiratory air sample undergoing investigation, and wherein the optical absorption signal comprises a spectral background signal. A second harmonic signal is isolated from the optical absorption signal and the period of the spectral background signal is identified. The second harmonic signal is sampled at a central wavelength of the second harmonic signal, wherein the central wavelength represents a maximum Carbon Dioxide absorption, and at an off-center wavelength of the second harmonic signal, wherein the off-center wavelength and the central wavelength are separated by a multiple of the period of the spectral background signal. A filtered capnography signal is then generated based on the sampled second harmonic signal.

Figure 1:
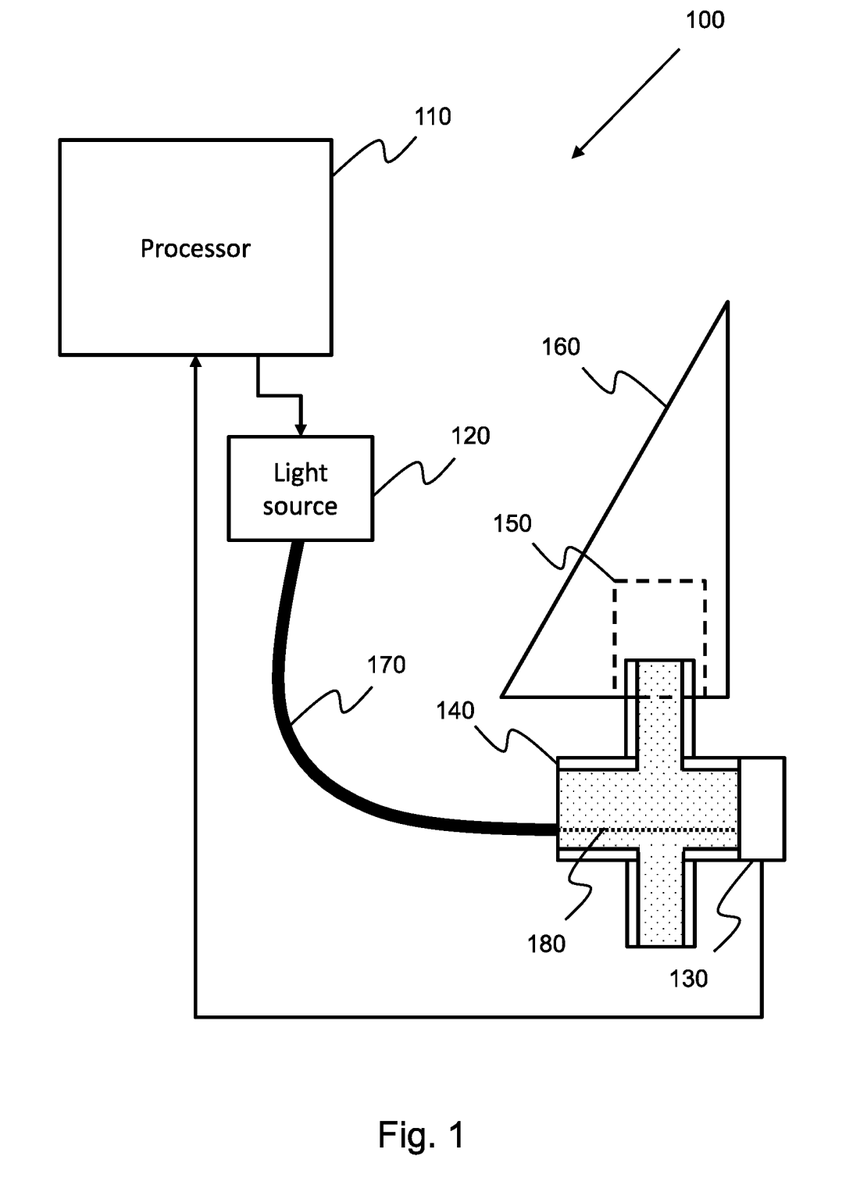
FIG. 1 shows a schematic representation of a laser based capnography system.

FIG. 1 shows a schematic representation of a laser based capnography system 100 according to an aspect of the invention.

The capnography system 100 shown in FIG. 1 comprises a processor 110 in communication with a laser light source 120 and a light detector 130. The light source 120 is in optical communication with a breathing adapter 140, disposed within a respiratory pathway 150 of a subject 160

The light source 120 is optically connected to the breathing adapter 140 by way of an optical fiber 170. The light source 120 may generate light of any wavelength suitable for performing capnography, such as light in the near-infrared range. For example, the light source 120 may be a Vertical Cavity Surface Emitting Laser (VCSEL) or Distributed Feedback (DFB) Laser.

The light source generates a beam of light 180, which passes through the optical fiber 170 and the breathing adapter 140 before impacting with the light detector 130. As the beam of light 180 passes through the breathing adapter 140, light is partially absorbed by Carbon Dioxide in the breathing adapter, thereby reducing the amount of light reaching the light detector 130, resulting in a lower detected light intensity compared to the intensity of the light beam at the laser light source. The difference in light intensity is then used to determine the concentration of the $CO_2$ in the breathing adapter and so in the respiratory air exhaled by the subject.

In particular, capnography systems such as the system 100 shown in FIG. 1 may include a VCSEL emitting at a wavelength close to 2 μm as a light source 120 and adapted to determine a concentration of $CO_2$ in the breathing adapter 140 in the form of a nasal cannula, oral-nasal cannula or airway adapter in a ventilation circuit.

Instead of having the light detector positioned on the breathing adapter, a second optical fiber can be used to guide the transmitted light to a light detector close the processor 110 or a single fiber can be used to guide the light to and from the breathing adapter using a retro-reflector inside the breathing adapter.

Figure 2:
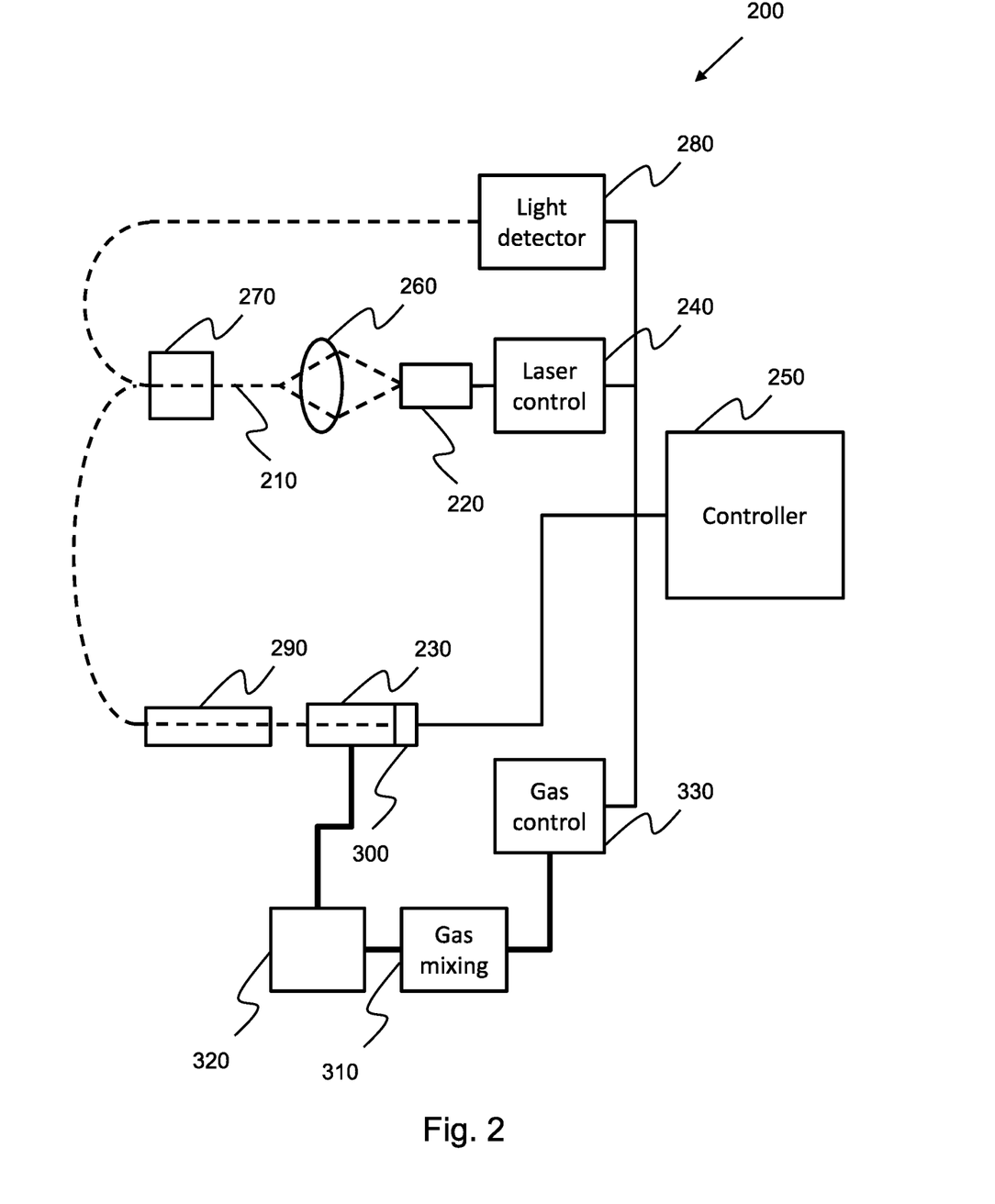
FIG. 2 shows a schematic representation of a system for the study of Tunable Diode Laser Absorption Spectroscopy with a fiber light guide.

FIG. 2 shows a schematic representation of a system 200 for the study of Tunable Diode Laser Absorption Spectroscopy with a fiber light guide (Fiber-TDLAS), which was used to obtain the measurement signals described below and is described here for the purpose of providing context to those results.

In the system 200 shown in FIG. 2, an optical fiber 210 is used to guide the light from the Vertical Cavity Surface Emitting Laser (VCSEL) 220 to the nasal cannula 230. The VCSEL is controlled and driven by a laser control 240, which is in communication with a central control unit 250. The laser control provides output signals for wavelength control and wavelength modulation to the VCSEL.

The system includes a VCSEL-to-fiber coupling unit 260, which focuses light from the VCSEL into the core of the optical fiber 210. A fiber splitter 270 guides a portion of the light, for example 10%, towards a reference photo detector 280 and the remaining light is guided through a patch cable 290 to the nasal cannula 230, which comprises a light detector 300. The light detector 300 may be an InGaAs light detector. By providing a separate photo detector 280, it is possible to evaluate and compensate for the spectral background and environmental $CO_2$ absorption in the VCSEL-to-fiber coupling unit 260.

The patch cable 290 incorporates a Single Mode (SM) fiber, a standard optical connector on one side and a special connector incorporating a gradient index (GRIN) lens on the other end. The light detector 300 of the nasal cannula 230 is connected to the central control unit 250.

The nasal cannula 230 is connected to a gas mixing station 310 with mass flow controllers to mix $CO_2$, $O_2$ and $N_2$ into a gas stream with varying $CO_2$ concentrations. To evaluate the dynamic behavior of the system, a response time fixture 320 is placed between the gas mixing station and the nasal cannula. The gas mixing station is controlled by a gas controller 330, which is in communication with the central controller 250.

The central controller 250 may control the gas composition through the gas controller 330 and the VCSEL power and wavelength as function of time through the laser controller 240.

In use, the wavelength of the light generated by the VCSEL 220 is slowly tuned (the time scale being in the order of seconds and above) by changing the VCSEL temperature with a miniature Thermo Electric Cooling (TEC) unit within the VCSEL housing and more rapidly via the injection current at rates that may extend into the region of 100 kHz. The TEC and temperature sensor monitoring the temperature of the VCSEL are connected to the laser control 240.

Both the slow tuning method and the rapid tuning method influence the power of the light emitted from the VCSEL, which may be referred to as Residual Amplitude Modulation (RAM). By controlling the TEC temperature, the wavelength of the light emitted by the VCSEL may be set close to the desired absorption line, i.e. the absorption line of the $CO_2$ gas relevant to capnography.

The tuning scheme described above may be used to select a specific absorption line, scan over an absorption line, or determine, during a certain time interval, the signal strength at a specific wavelength. In addition, an AC current modulation may be applied to the VCSEL, giving a sinusoidal modulation of the emission wavelength of the generated light beam, which acts as a dither over the absorption line and enables lock-in detection. The AC current modulation may be referred to as Wavelength Modulation Spectroscopy (WMS) and improves the signal-to-noise ratio and zero stability of the measurements compared to direct absorption measurements. WMS is relevant for capnography measurements in the weak 2 μm absorption region of $CO_2$ in combination with the limitation of a short absorption path in the capnography nasal cannula 230.

The first harmonic of the measurement signal is the most sensitive to RAM offset; whereas, the second harmonic $f_2$ and third harmonic $f_3$ have a significantly smaller RAM contribution. The $f_2$ signal provides the $CO_2$ concentration in the nasal cannula and the $f_3$ signal, with a zero crossing at the center of the absorption line, may be used in a feedback loop for wavelength stabilization. The $f_2$ and $f_3$ signals may be normalized to the DC level ($f_0$) to remove the dependence of the measurements on the emission power of the VCSEL.

As discussed above, the detection sensitivity of the capnography system 200 is limited by spectral background in the optical absorption signal, i.e. the optical interference fringes, rather than the theoretical sensitivity limit given by detector shot noise. In order to resolve gas absorption lines in TDLAS, the use of lasers with a narrow emission linewidth is required. A consequence of the narrow linewidth is the long coherence length, which introduces interference effects. Typical spacing of interfaces contributing to interference within the nasal cannula 230 and optical components within the VCSEL-to-fiber coupling unit 260 lead to fringe modulation periods comparable to the absorption line width. Unfortunately, WMS does not only enhance the absorption feature but also the fringe features.

During respiration, fluctuations in temperature and/or vibrations, for example from the breathing motion and temperature variations in the respiratory flow of the patient, cause the interference fringes to shift in wavelength such that they cannot be removed by simple subtraction of a baseline signal. However, the wavelength period of the interference fringe is much less sensitive to fluctuations in temperature and vibrations.

Figure 3:
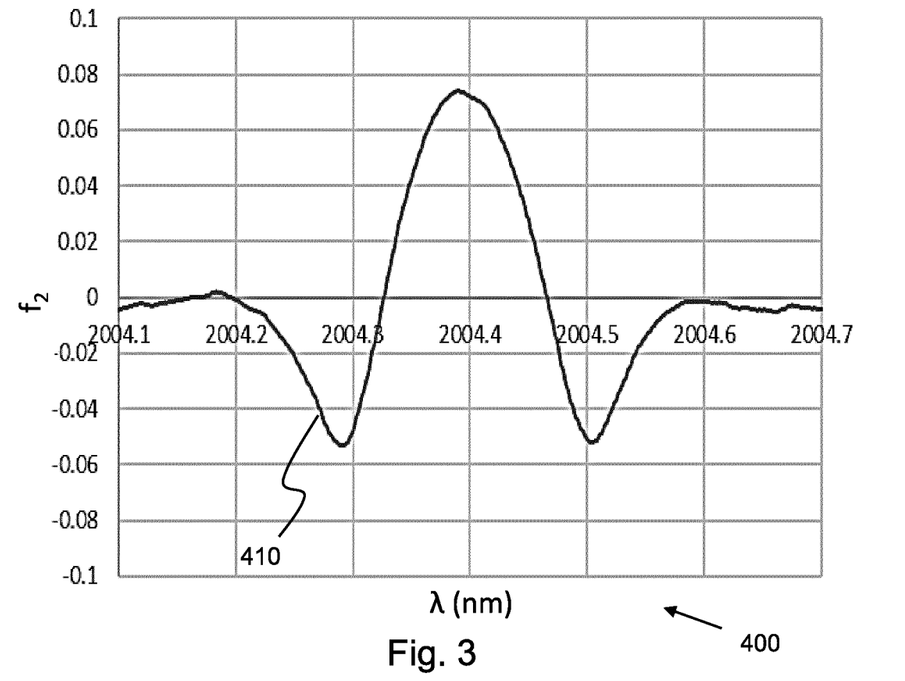
FIG. 3 shows a graph of signal amplitude against wavelength for the second harmonic $CO_2$ absorption line signal.

FIG. 3 shows a graph 400 of signal amplitude against wavelength (λ) for the second harmonic ($f_2$) $CO_2$ absorption line signal 410 with spectral background oscillations resulting from interference in the gas sensing cavity within the breathing adapter.

Spectral background prevents fiber-TDLAS from reaching the +2 mmHg (±0.27 kPa) accuracy required for capnography with an absorption path length of roughly 1 cm within the nasal cannula. As the spectral background period is comparable to the absorption line feature, known methods for spectral background suppression, such as decomposition in the frequency domain, are inaccurate. Other known methods require significant processing time, which is incompatible with the capnography requirement of a roughly 100 ms time response to $CO_2$ concentration changes to be able to acquire an accurate capnography waveform during exhalation.

More specifically, FIG. 3 shows the second harmonic ($f_2$) $CO_2$ absorption line and spectral background signals around 2004.4 nm wavelength using the setup and WMS method described above with reference to FIG. 2. The absorption path in the breathing adapter cavity used to acquire the measurement shown in FIG. 3 was 7.5 mm and the $CO_2$ concentration was 55 mmHg (7.3 kPa). The spectral background oscillations resulting from interferences in the breathing adapter are present all over the line 410, but are particularly visible in the wings, i.e. away from the central peak.

Figure 4:
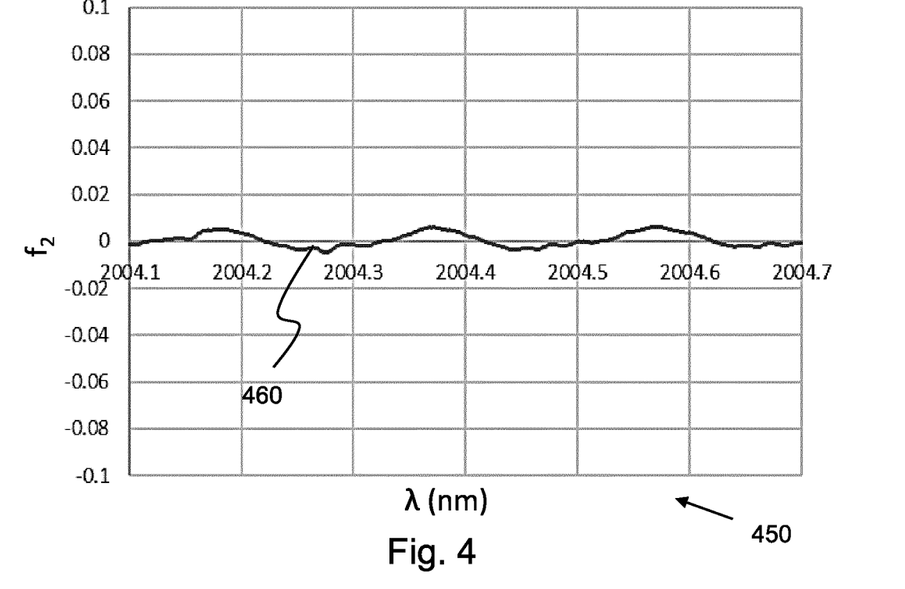
FIG. 4 shows a graph of signal amplitude against wavelength for the second harmonic signal for only the spectral background.

FIG. 4 shows a graph 450 of signal amplitude against wavelength (λ) for the second harmonic ($f_2$) for only the spectral background 460 when pure Nitrogen gas flows through the cavity of the breathing adapter. For the measurement shown, the peak-to-peak spectral background corresponds to ±4 mmHg (±0.53 kPa) $CO_2$, i.e. twice the accuracy required for capnography.

The spectral background suppression method described herein is based on sampling the measured capnography signal and the spectral background at multiple wavelengths, determined by the spectral background period. A more detailed explanation of the method is provided further below.

One sampling takes place at a central wavelength of the second harmonic (i.e. the position of maximum $CO_2$ absorption), or third harmonic (zero crossing), of the capnography signal, while at least one other sampling takes place at a half multiple, or a whole multiple, of the spectral background period away from the central wavelength. By addition or subtraction of the sampled signals, the spectral background signal may be suppressed and a background free absorption signal strength may be obtained, thereby providing an accurate measure of the $CO_2$ concentration. The resulting value is independent of the wavelength shift of the spectral background due to fluctuations, for instance due to temperature changes, as the sampling at the various wavelengths occurs at a time scale that is fast compared to these fluctuations. The resulting value is also independent of the spectral background intensity.

Further, in addition to sampling at the central wavelength of the second harmonic, additional samples taken at two, or more, off-center wavelengths one spectral background period away on both sides of the central frequency.

A significant amount of the sampling time, for instance 50%, is focused at the central wavelength, which means that there is limited loss in signal accuracy for $CO_2$ detection by this spectral background suppression method. The spectral background suppression method requires limited processing power, thereby enabling real time $CO_2$ measurements during respiration.

For example, a first sampling may take place at one spectral background period below the central wavelength of the second harmonic, followed by a sampling at the central wavelength and finally sampling takes place at one spectral background period above the central wavelength. The time for sampling at the central wavelength and at the off-center wavelengths may be equally divided, which typically results in the highest signal-to-noise in the determination of the $CO_2$ concentration; however, different ratios may also be applied.

Figure 5:
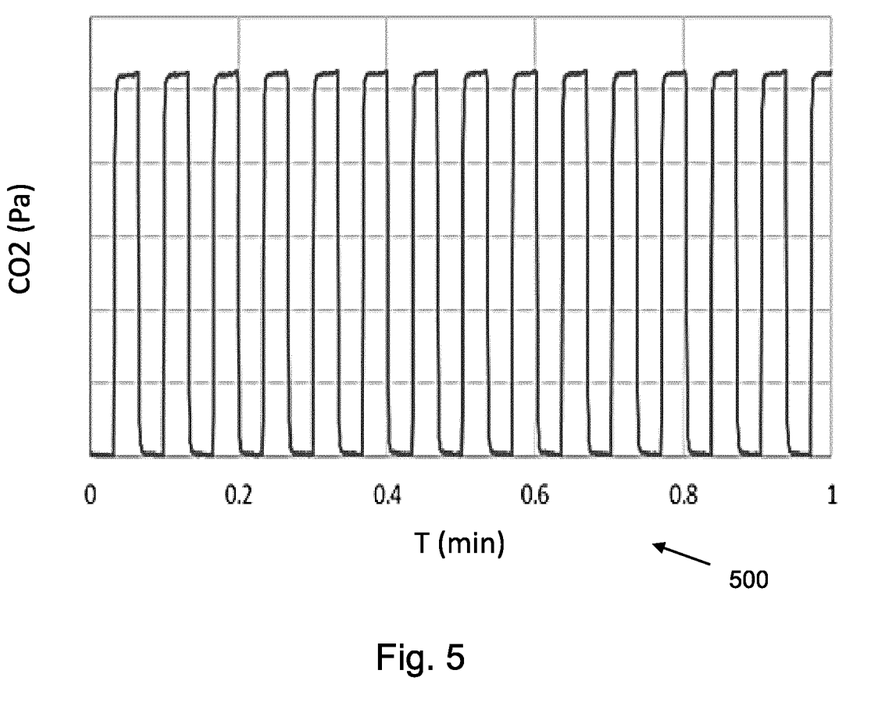
FIG. 5 shows a capnogram resulting from a square wave modulation in $CO_2$ concentration after spectral background suppression has been performed.

FIG. 5 shows a capnogram 500 resulting from a square wave modulation in $CO_2$ concentration and after spectral background suppression as described above has been performed. For this measurement, one wavelength was set at the central wavelength of the second harmonic signal of the capnography signal, i.e. the $f_2$ maximum, and another wavelength was set at one spectral background period away from the $f_2$ maximum where the absorption strength is small. As can be seen from FIG. 5, the capnogram shows stable zero and maximum levels and a fast response to $CO_2$ changes.

Looking to the spectral background suppression in more detail, the $f_2$ signal strength at the central wavelength, corrected for the spectral background, results from the following equations:

$$f_2(0)-0.5\{f_2(-p_{sb})+f_2(p_{sb})\}=f_{2,sb}(0)-0.5\{f_{2,sb}(-p_{sb})+f_{2,sb}(p_{sb})\}$$

$$f_2(0)-f_2(p_{sb})=\{1-k\}f_2(0)=f_{2,sb}(0)-0.5\{f_{2,sb}(-p_{sb})+f_{2,sb}(p_{sb})\}$$

and is given by:

$$f_2(0)=\{f_{2,sb}(0)-0.5\{f_{2,sb}(-p_{sb})+f_{2,sb}(p_{sb})\}\}/\{1-k\}$$

wherein: $f_2(x)$ and $f_{2,sb}(x)$ are the second harmonic signals as a function of normalized wavelength (x) without and with spectral background, respectively. The normalized wavelength is given by the difference of the wavelength with respect to the central wavelength and is normalized to the linewidth. The ratio k is given by the function:

$$k=f_2(p_{sb})/f_2(0)=H_2(p_{sb},m)/H_2(0,m)$$

wherein: $p_{sb}$ is the spectral background period; and $H_2(x, m)$ is the second harmonic line shape function given by:

$$H_2(x, m) = \frac{\sqrt{2M(x, m) + 2r(x, m)}\{2r(x, m) - m^2\}}{m^2 r(x, m)} - \frac{4}{m^2}$$

with $M(x, m)=1+m^2-x^2$ and $r(x, m)=\sqrt{\{1+m^2-x^2\}^2+4x^2}$, wherein: m is the normalized WMS modulation depth given by the ratio of modulation amplitude divided by the absorption linewidth.

Alternatively, when considered within a capnography system, such as the systems described above, the spectral background period is relatively constant, meaning a signal $F_2$ may be defined as:

$$F_2=\{1-k\}f_2(0)=\{f_{2,sb}(0)-0.5\{f_{2,sb}(-p_{sb})+f_{2,sb}(p_{sb})\}\}$$

wherein $F_2$ is calibrated against the $CO_2$ concentration. In subsequent measurements of the $CO_2$ concentration, the calculated $F_2$ from $f_{2,sb}(-p_{sb})$, $f_{2,sb}(0)$, $f_{2,sb}(p_{sb})$ and the slope resulting from the calibration may be used to determine the $CO_2$ concentration. In this case, the k value and line shape function $H_2(x, m)$ described above are no longer required.

Following the spectral background suppression, the corrected second harmonic signal is independent of spectral background magnitude and wavelength shift. The advantage of using multiple off-center wavelength samples over the scheme with 1 off-center wavelength sample is that the final second harmonic signal is also robust against small changes in the spectral background period. However, at larger fluctuations in the spectral background period the corrected second harmonic signal, where the spectral background has been suppressed, may become sensitive to spectral background wavelength shifts.

For performing the spectral background suppression, there is at least a signal sampling at one off-center wavelength. Sampling at one off-center wavelength, or a small number of off-center wavelengths, has the advantage of a shorter sampling time over a larger number of samples and by that, a better signal-to-noise ratio; whereas a larger number of off-center wavelength samples may offer more effective spectral background suppression. Accordingly, the number of off-center wavelength samples may be adjusted according to the application of the spectral background suppression method.

If the third harmonic signal $f_3$ is used for wavelength stabilization of the VCSEL, the $f_3$ signal may also be corrected for spectral background signals in a similar way as described above using the third harmonic line shape function $H_3(x, m)$ instead of $H_2(x, m)$.

In the examples described above, the sampling of the off-center wavelengths is performed at wavelengths that differ from the central wavelength by one, or a multiple of one, spectral background period. Alternatively, the sampling of the off-center wavelengths may also be performed at wavelengths that differ from the central wavelength by one half, or a multiple of one half, of the spectral background period. For detection at two off-center wavelength that are half a spectral background period away from the central wavelength, the expression for the spectral background corrected $f_2$ signal becomes:

$$f_2(0)=\{f_{2,sb}(0)+0.5\{f_{2,sb}(-p_{sb})+f_{2,sb}(p_{sb})\}\}/\{1+k\}$$

with $$k=f_2(0.5p_{sb})/f_2(0)=H_2(0.5p_{sb},m)/H_2(0,m)$$

It should be noted that, for sampling at a half multiple spectral background period, a sign has changed in the expression compared to sampling at a full multiple spectral background period.

The spectral background period is determined by the interference path length of the capnography system. With a VCSEL-to-fiber unit, as described above with reference to FIG. 2, with negligible spectral background, or the use of a reference detector at the VCSEL unit for spectral background suppression, the dominant spectral background in the measured capnography signal results from optical interference by reflections at optical interfaces in the nasal cannula or airway adapter in a subject ventilation circuit. Replacement of this component, which in practice is a disposable component, may lead to a change in spectral background period.

In capnography, the relevant information is obtained from the capnogram in the exhalation phase of the breathing cycle and from the respiration rate. This means that the inhalation phase may be used to derive the spectral background period, without interrupting the measurements performed in the exhalation phase. During the inhalation phase, environmental air is inhaled with a much lower $CO_2$ concentration than the air exhaled by the subject, meaning the spectral background signal is more pronounced during the inhalation phase than during the exhalation phase.

During at least part of the inhalation phase, a linear wavelength sampling sweep may be performed, followed by an analysis of the signal for the spectral background period. The analysis may be performed by fitting with a sinusoidal curve, or by performing a Fourier analysis, to determine the dominant frequency in the obtained inhalation phase signal. Averaging may be performed over multiple inhalation periods to further improve accuracy of the spectral background period.

As stated above, the spectral background period is dependent on the optical light path of the system and reflections in the breathing adapter. At larger WMS modulation amplitudes, the width of the $f_2$ line and the spacing of the $f_2$ minima is determined by the modulation amplitude. This combination can be exploited to position the off-center wavelength samples at a favorable position on the $f_2$ line.

For example, if the spectral background period is large compared to the $f_2$ line width and the intensity at the wing of the $f_2$ line for the off-center wavelength sample is negligible, the above formulas simplify because k=0, thereby simplifying the calculations required to suppress the spectral background signal.

Alternatively, the modulation depth and/or the dimensions of the breathing adapter may be selected such that the spectral background period corresponds to the spacing between a minimum and a maximum of the $f_2$ line, in which case:

$$F_2 = f_2(0) - 0.5\{f_2(-p_{sb}) + f_2(p_{sb})\} =$$
$$f_2^{maximum} - 0.5\{f_2^{left\ minimum} + f_2^{right\ minimum}\} =$$
$$\{f_{2,sb}(0) - 0.5\{f_{2,sb}(-p_{sb}) + f_{2,sb}(p_{sb})\}\}$$

As $f_2^{left\ minimum}$ and $f_2^{right\ minimum}$ have opposite signs with respect to $f_2^{maximum}$ and correspond to the largest magnitude points on the $f_2$ line. Sampling at these positions may maximize the signal-to-noise ratio of the filtered $f_2$ signal and result in an improved accuracy for $CO_2$ concentration detection.

Figure 6:
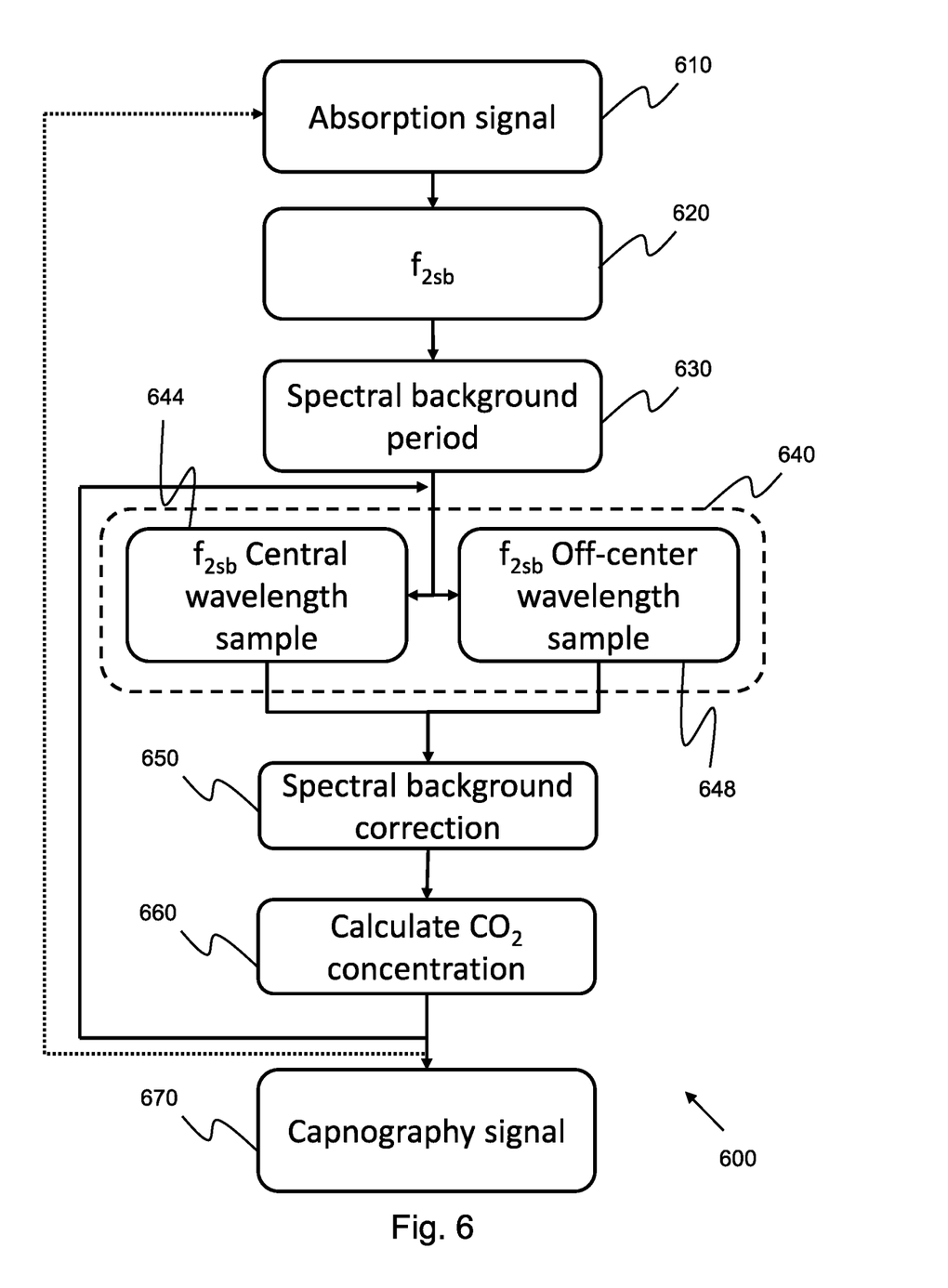
FIG. 6 shows a method of the invention.

FIG. 6 shows a method 600 for obtaining a filtered capnography signal by suppressing a spectral background signal within an optical absorption signal.

The method begins in step 610 by obtaining an optical absorption signal from a subject across a range of wavelengths, wherein the optical absorption signal represents a proportion of a light signal that is absorbed as the light signal passes through a breathing adapter containing a respiratory air sample undergoing investigation, and wherein the optical absorption signal comprises a spectral background signal. The optical absorption signal may be obtained directly from a nasal cannula, or any other device for obtaining a gas sample from a subject. Alternatively, the optical absorption signal may be obtained from a memory of a processing system, meaning that the spectral background signal suppression may be performed by any suitable processing system.

In step 620, a second harmonic signal is isolated from the optical absorption signal and in step 630, a period of the spectral background signal is identified.

In step 640, a plurality of wavelength components of the second harmonic signal are sampled, wherein sampling the second harmonic signal comprises: obtaining 644 a sample of the second harmonic signal at a central wavelength of the second harmonic signal, wherein the central wavelength represents a maximum Carbon Dioxide absorption; and obtaining 648 a sample of the second harmonic signal at an off-center wavelength of the second harmonic signal, wherein the off-center wavelength and the central wavelength are separated by a multiple of the period of the spectral background signal.

In step 650, a spectral background correction is calculated at the central wavelength based on the sampled second harmonic samples from step 640.

In step 660, the $CO_2$ concentration is calculated based on the absorption sample with the spectral background correction applied.

Steps 640, 650 and 660 are repeated to generate, in step 670, a time series of $CO_2$ concentration values, which provides the filtered capnography signal. A single loop of steps 640, 650 and 660 may take, for example, 100 ms, which would result in the time series of $CO_2$ concentration values comprising a stream of $CO_2$ values every 100 ms.

When spectral background period variations are present and a regular adjustment of the spectral background period is necessary to improve system performance, steps 610, 620 and 630 may also be repeated in a feedback loop. Such a spectral period adjustment may take place at a time scale that is long compared to the time it takes to go through the capnography signal generation loop of steps 640, 650 and 660.

Figure 7:
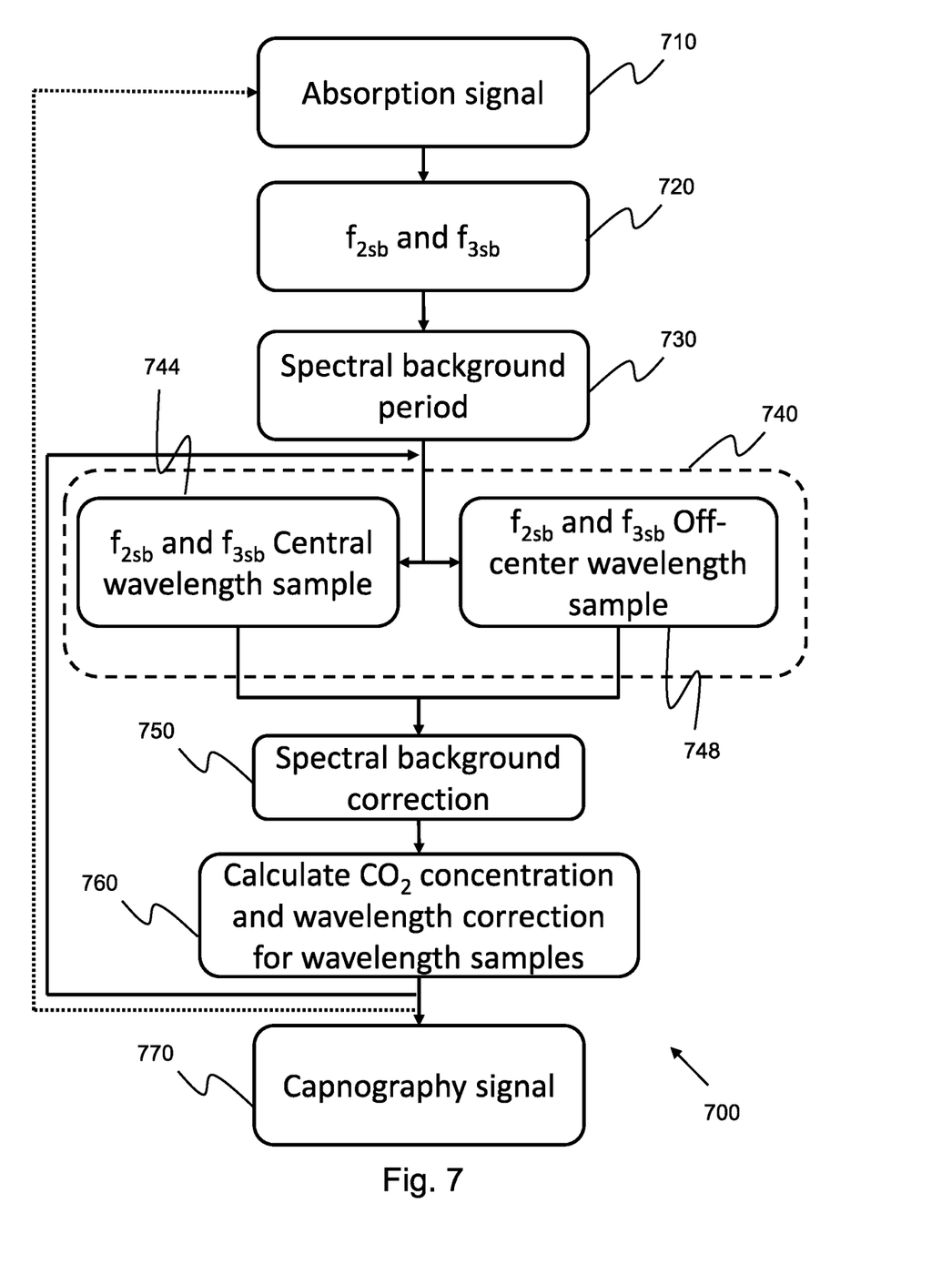
FIG. 7 shows a method of the invention including a feedback loop for wavelength control.

FIG. 7 shows a method 700 for obtaining a filtered capnography signal by suppressing a spectral background signal within an optical absorption signal based on a second harmonic and a third harmonic of the optical absorption signal.

The method begins in step 710 by obtaining an optical absorption signal from a subject across a range of wavelengths, wherein the optical absorption signal represents a proportion of a light signal that is absorbed as the light signal passes through a breathing adapter containing a respiratory air sample undergoing investigation, and wherein the optical absorption signal comprises a spectral background signal. The optical absorption signal may be obtained directly from a nasal cannula, or any other device for obtaining a gas sample from a subject. Alternatively, the optical absorption signal may be obtained from a memory of a processing system, meaning that the spectral background signal suppression may be performed by any suitable processing system.

In step 720, a second harmonic signal and a third harmonic signal are isolated from the optical absorption signal and in step 730, a period of the spectral background signal is identified.

In step 740, a plurality of wavelength components of the second harmonic signal and the third harmonic signal are sampled, wherein sampling the harmonic signals comprises: obtaining 744 a sample of the harmonic signals at a central wavelength of the harmonic signals; and obtaining 748 a sample of the harmonic signals at an off-center wavelength of the harmonic signals, wherein the off-center wavelength and the central wavelength are separated by a multiple of the period of the spectral background signal. During signal processing an absorption signal sample at a specific wavelength can be used to generate both the second harmonic and third harmonic sample.

In step 750, a spectral background correction is calculated for both the second harmonic as well as third harmonic at the central wavelength based on the samples from step 740.

In step 760, the $CO_2$ concentration is calculated based on the absorption signal with the spectral background correction applied and a wavelength correction is calculated based on the sample third harmonic signal. The wavelength correction is applied in a subsequent loop step to adjust the wavelengths for the sampling in step 740.

In step 770, a filtered capnography signal is generated based on the calculated $CO_2$ concentrations.

In addition, the method 700 of FIG. 7 may include similar feedback loops to those described above with reference to FIG. 6.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for obtaining a filtered capnography signal by suppressing a spectral background signal within an optical absorption signal, the method comprising:
   obtaining the optical absorption signal from a subject across a range of wavelengths, wherein the optical absorption signal represents a proportion of a light signal that is absorbed as the light signal passes through a breathing adapter containing a respiratory air sample undergoing investigation, and wherein the optical absorption signal comprises the spectral background signal;
   isolating a second harmonic signal from the optical absorption signal;
   identifying a period of the spectral background signal;
   sampling a plurality of wavelength components of the second harmonic signal, wherein sampling the second harmonic signal comprises:
   obtaining a sample of the second harmonic signal at a central wavelength of the second harmonic signal, wherein the central wavelength represents a maximum Carbon Dioxide absorption; and
   obtaining a sample of the second harmonic signal at an off-center wavelength of the second harmonic signal, wherein the off-center wavelength and the central wavelength are separated by a half or whole non-zero multiple of the period of the spectral background signal; and
   generating a filtered capnography signal based at least in part on an additive or subtractive combination of the obtained sample of the second harmonic signal.

2. A method as claimed in claim 1, wherein obtaining the sample of the second harmonic signal at the central wavelength is performed over a first time period and obtaining the sample of the second harmonic signal at the off-center wavelength is performed over a second time period, wherein the first time period and the second time period are equal in length.

3. A method as claimed in claim 1, wherein sampling the second harmonic signal further comprises obtaining a plurality of samples of the second harmonic signal at a plurality of off-center wavelengths of the second harmonic signal, wherein the plurality of off-center wavelengths and the central wavelength are separated by multiples of the period of the spectral background signal.

4. A method as claimed in claim 3, wherein obtaining the sample of the second harmonic signal at the central wavelength is performed over a first time period and obtaining the plurality of samples of the second harmonic signal at the plurality of off-center wavelengths is performed over a second time period, wherein the first time period and the second time period are equal in length.

5. A method as claimed in claim 1, wherein the method further comprises:
   isolating a third harmonic signal from the optical absorption signal;
   sampling a plurality of wavelength components of the third harmonic signal, wherein sampling the third harmonic signal comprises:
   obtaining a sample of the third harmonic signal at a central wavelength of the third harmonic signal; and
   obtaining a sample of the third harmonic signal at an off-center wavelength of the third harmonic signal, wherein the off-center wavelength and the central frequency are separated by a multiple of the period of the spectral background signal; and
   generating a wavelength correction for the central and off-center wavelengths.

6. A method as claimed in claim 1, wherein the method is for use in processing an optical absorption signal obtained from a breathing cycle of a subject.

7. A method as claimed in claim 6, wherein the period of the spectral background signal is identified during an inhalation phase of the breathing cycle.

8. A method as claimed in claim 6, wherein the period of the spectral background signal is identified by averaging over a plurality of breathing cycles.

9. A method as claimed in claim 1, wherein the method further comprises obtaining a separate background signal, wherein the spectral background period is identified from the separate background signal.

10. A computer program comprising computer program code means which is adapted, when said computer program is run on a computer, to implement the method of claim 1.

11. A system for obtaining a filtered capnography signal by suppressing a spectral background signal within an optical absorption signal, the system comprising:
    a processor, wherein the processor is adapted to:
    obtain the optical absorption signal from a subject across a range of wavelengths, wherein the optical absorption signal represents a proportion of a light signal that is absorbed as the light signal passes through a breathing adapter containing a respiratory air sample undergoing investigation, and wherein the optical absorption signal comprises the spectral background signal;
    isolate a second harmonic signal from the optical absorption signal;
    identify a period of the spectral background signal;
    sample a plurality of wavelength components of the second harmonic signal, wherein sampling the second harmonic signal comprises:
    obtaining a sample of the second harmonic signal at a central wavelength of the second harmonic signal, wherein the central wavelength represents a maximum Carbon Dioxide absorption; and
    obtaining a sample of the second harmonic signal at an off-center wavelength of the second harmonic signal, wherein the off-center wavelength and the central wavelength are separated by a half or whole non-zero multiple of the period of the spectral background signal; and
    generate a filtered capnography signal based at least in part on an additive or subtractive combination of the obtained sample of the second harmonic signal.

12. A system as claimed in claim 11, wherein the system further comprises:
    a processor as claimed in claim 11;
    a wavelength tunable laser light source adapted to generate a laser light signal that is modulated across a range of wavelengths, and wherein the processor is further adapted to isolate the second harmonic signal using a frequency of the modulation of the light source as a reference;
    an optical fiber in communication with the wavelength tunable laser light source;

a breathing adapter having a cavity adapted to be connectable to an airway of a subject, the breathing adapter being in communication with the optical fiber such that the laser light signal enters the cavity; and a light detector, in communication with the cavity of the breathing adapter and adapted to receive the laser light signal transmitted through the cavity.

13. A system as claimed in claim 11, wherein one or more of:

the modulation depth of the light source; and a dimension of the breathing adapter, is adjusted, thereby adjusting the spectral background period, in order to align the spectral background period with a maximum and a minimum of second harmonic signal.

* * * * *